(12) United States Patent
Stoehr

(10) Patent No.: US 7,794,987 B2
(45) Date of Patent: Sep. 14, 2010

(54) METHOD FOR TREATING CENTRAL NEUROPATHIC PAIN

(75) Inventor: Thomas Stoehr, Monheim (DE)

(73) Assignee: UCB Pharma GmbH, Monheim (DE)

( * ) Notice: Subject to any disclaimer, the term of this patent is extended or adjusted under 35 U.S.C. 154(b) by 251 days.

(21) Appl. No.: 11/000,951

(22) Filed: Dec. 2, 2004

(65) Prior Publication Data

US 2005/0209163 A1  Sep. 22, 2005

Related U.S. Application Data

(60) Provisional application No. 60/530,895, filed on Dec. 22, 2003.

(30) Foreign Application Priority Data

Dec. 2, 2003 (EP) ................... 03027742
Dec. 22, 2003 (EP) ................... 03029632

(51) Int. Cl.
*C12P 13/04* (2006.01)
*A61B 19/00* (2006.01)
*A61K 37/18* (2006.01)

(52) U.S. Cl. .......................... 435/106; 600/557; 514/2; 530/300

(58) Field of Classification Search .................. None
See application file for complete search history.

(56) References Cited

U.S. PATENT DOCUMENTS

| | | | |
|---|---|---|---|
| 5,378,729 A | 1/1995 | Kohn et al. | 514/231.2 |
| 5,585,358 A | 12/1996 | Bialer et al. | 514/19 |
| 5,654,301 A | 8/1997 | Kohn et al. | 514/231.2 |
| 5,760,038 A | 6/1998 | Murugesan et al. | 514/252 |
| 5,885,999 A | 3/1999 | Elliott et al. | 514/258 |
| 6,001,876 A | 12/1999 | Singh | 514/561 |
| 6,037,324 A | 3/2000 | Schwender et al. | 514/18 |
| 6,048,899 A | 4/2000 | Kohn et al. | 514/626 |
| 6,083,941 A * | 7/2000 | Farb | 514/177 |
| 6,083,951 A | 7/2000 | Bradbury | 514/256 |
| 6,114,390 A | 9/2000 | Engel et al. | 514/595 |
| 6,133,261 A | 10/2000 | Harris | 514/231.2 |
| 6,277,825 B1 | 8/2001 | Olivera et al. | 514/13 |
| 6,331,637 B1 | 12/2001 | Chan et al. | 548/241 |
| 6,492,553 B1 | 12/2002 | Hulme et al. | 564/129 |
| 6,737,408 B1 | 5/2004 | Balasubramanium et al. | 514/18 |
| RE38,551 E | 7/2004 | Kohn | 514/616 |
| 6,803,481 B2 | 10/2004 | Selve | 560/157 |
| 6,884,910 B2 * | 4/2005 | Harris | 562/553 |
| 7,148,378 B2 | 12/2006 | Harris | 562/553 |
| 7,186,859 B2 | 3/2007 | Harris | 562/553 |
| 7,416,864 B2 | 8/2008 | Stoehr | 435/106 |
| 2002/0052418 A1 | 5/2002 | Shirvan et al. | 514/626 |
| 2002/0058683 A1 | 5/2002 | Tinembart et al. | 514/357 |
| 2002/0086828 A1* | 7/2002 | Harris | 514/12 |
| 2002/0169174 A1 | 11/2002 | Chackalamannil et al. | 514/262.1 |
| 2003/0216466 A1 | 11/2003 | Scheuerman et al. | 514/513 |
| 2004/0101582 A1 | 5/2004 | Wolicki | 424/760 |
| 2004/0204495 A1 | 10/2004 | Shirvan et al. | 514/616 |
| 2004/0220077 A1 | 11/2004 | Selve | 514/1 |
| 2005/0227961 A1 | 10/2005 | Kucharik et al. | 514/211.13 |
| 2005/0288234 A1 | 12/2005 | Stoehr | 514/19 |
| 2006/0046957 A1 | 3/2006 | Beyreuther et al. | 514/7 |
| 2006/0100157 A1 | 5/2006 | Rauschkolb-Loffler et al. | 514/18 |
| 2006/0135437 A1 | 6/2006 | Stoehr et al. | 514/19 |
| 2006/0252749 A1 | 11/2006 | Stohr | 514/220 |
| 2007/0042969 A1 | 2/2007 | Rauschkolb-Loffler et al. | 514/19 |
| 2007/0043120 A1 | 2/2007 | Beyreuther et al. | 514/616 |
| 2007/0048372 A1 | 3/2007 | Beyreuther et al. | 424/464 |
| 2007/0054962 A1 | 3/2007 | Selve | 514/575 |
| 2007/0197657 A1 | 8/2007 | Beyreuther et al. | 514/616 |
| 2008/0027137 A1 | 1/2008 | Riedner et al. | 514/561 |
| 2008/0287545 A1 | 11/2008 | Scheller et al. | 514/616 |
| 2009/0018197 A1 | 1/2009 | Rudd et al. | 514/563 |
| 2009/0018198 A1 | 1/2009 | Stohr | 514/563 |

FOREIGN PATENT DOCUMENTS

| | | |
|---|---|---|
| EP | 0302389 | 2/1989 |
| EP | 0412849 | 2/1991 |
| EP | 0 555 537 | 8/1993 |
| EP | 0 885 186 | 12/1998 |
| EP | 0 997 147 | 5/2000 |
| EP | 1 077 945 | 2/2001 |
| EP | 1 160 248 | 12/2001 |
| EP | 1243263 | 9/2002 |
| EP | 1 486 205 | 12/2004 |
| EP | 1 486 206 | 12/2004 |
| EP | 1 537 862 | 6/2005 |
| EP | 1 541 138 | 6/2005 |

(Continued)

OTHER PUBLICATIONS

Morrow, 2001, Soc. Neuroscience Abstract No. 508.16, 1 page.*
[Retrived fromwebsite]: "http://www.helpforpain.com/arch2000dec.htm", 2000, 2 pages [retrieved on Dec. 2, 2007].*
[Retrived fromwebsite]:http://www.spineuniverse.com/displayarticle.php/article1614.html, 2007, 8 pages,[retrieved on Nov. 30, 2007.*
Hovinga, 2003, IDrugs, 6(5), 479-485.*
Morrow, et al., 2001, Soc Neuroscience, Abstract No. 508.16, 1 page.*
Mills, 2001, Journal of Neurotrauma, 18, 743-756.*
Retrived from: http://www.ncbi.nlm.nih.gov/books/bv.fcgi?rid=hstat1.chapter.64890, 2001, 12 pages [retrieved on Aug. 13, 2009].*

(Continued)

*Primary Examiner*—Andrew D Kosar
*Assistant Examiner*—Satyanarayana R Gudibande
(74) *Attorney, Agent, or Firm*—Harness, Dickey & Pierce, P.L.C.

(57) ABSTRACT

The present invention concerns the use of compounds for treating central neuropathic pain.

32 Claims, 2 Drawing Sheets

FOREIGN PATENT DOCUMENTS

Figure 1:
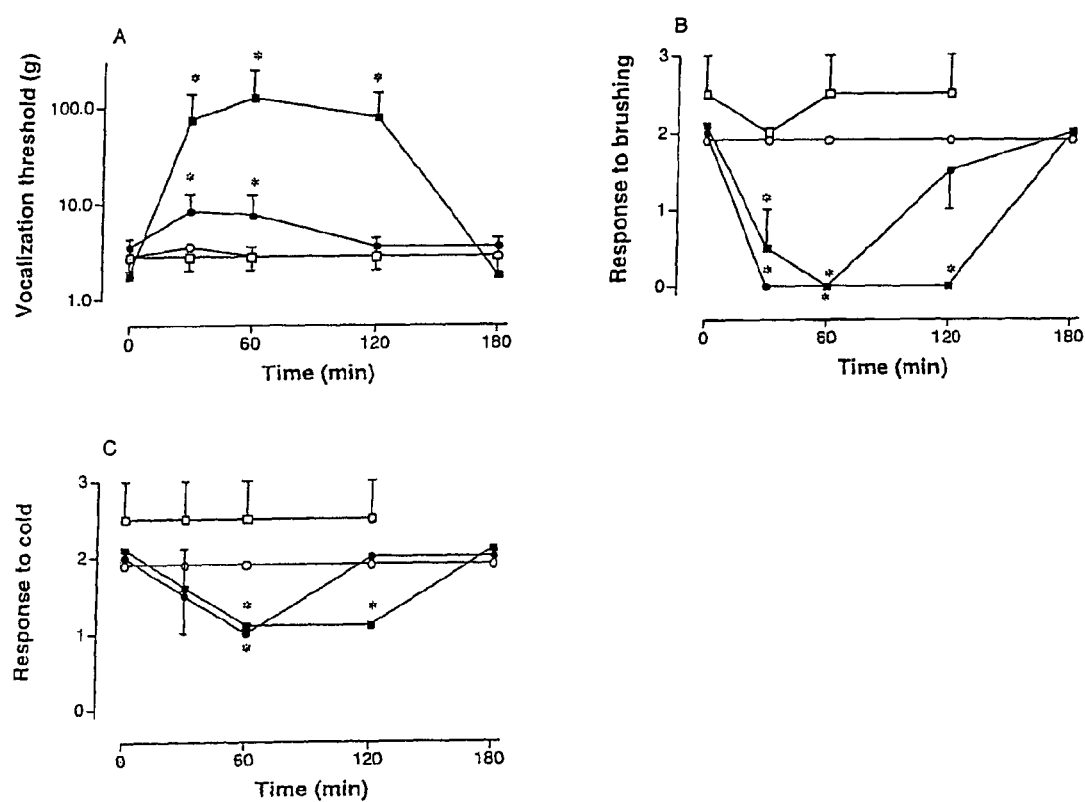

| | | |
|---|---|---|
| EP | 1 579 858 | 9/2005 |
| EP | 1 688 137 | 8/2006 |
| WO | WO 96/32100 | 10/1996 |
| WO | WO 9632100 | 10/1996 |
| WO | WO 99/07413 | 2/1999 |
| WO | WO 99/56761 | 11/1999 |
| WO | WO 00/21509 | 4/2000 |
| WO | WO 00/51586 | 9/2000 |
| WO | WO 01/17976 | 3/2001 |
| WO | WO 01/78762 | 10/2001 |
| WO | WO 02/13766 | 2/2002 |
| WO | WO 02/15922 | 2/2002 |
| WO | WO 02/15937 | 2/2002 |
| WO | WO 0215922 | 2/2002 |
| WO | WO 02/24698 | 3/2002 |
| WO | WO 02/42256 | 5/2002 |
| WO | WO 02/50051 | 6/2002 |
| WO | WO 02/060863 | 8/2002 |
| WO | WO 02/074297 | 9/2002 |
| WO | WO 02/076979 | 10/2002 |
| WO | WO 03/000642 | 1/2003 |
| WO | WO 03/039520 | 5/2003 |
| WO | WO 03/106482 | 12/2003 |
| WO | WO 2004/043926 | 5/2004 |
| WO | WO 2004/066987 | 8/2004 |
| WO | WO 2004/066990 | 8/2004 |
| WO | WO 2004/100871 | 11/2004 |
| WO | WO 2005/040355 | 5/2005 |
| WO | WO 2005/053667 | 6/2005 |
| WO | WO 2005/092313 | 10/2005 |
| WO | WO 2005/099740 | 10/2005 |
| WO | WO 2005/120539 | 12/2005 |

OTHER PUBLICATIONS

Hovinga Collin A, "SPM-927 (Schwarz Pharma)," Idrugs: The Investigational drugs Journal, England, May 2003, pp. 479-485, vol. 6, No. 5, XP001180322, ISSN: 1369-7056, p. 479, col. 1, line 54-col. 2, line 16; p. 480, col. 1, line 51-col. 2, line 6; p. 481, col. 2, line 10-26.
Abdulla & Smith (2002) J. Neurophysiol. 88:2518-2529.
Akiba et al. (2003) Receptors & Channels 9:291-299.
Amir et al. (2006) J. Pain 7(5 Suppl. 3):S1-S29.
Arnér & Meyerson (1988) Pain 33:11-23.
Arroyo (2003) "Safety of SPM 927 in subjects with epilepsy and neuropathic pain" Poster presented at AES Scientific Exhibit, Dec. 5-10, 2003.
Backonja (2002) Neurology 59:S14-S17.
Backonja (2003) Anesth. Analg. 97:785-790.
Béguin et al. (2003) Bioorganic & Medicinal Chemistry 11:4275-4285.
Béguin et al. (2004) Bioorganic & Medicinal Chemistry 12:3079-3096.
Bennett & Xie (1988) Pain 33(1):87-107 (abstract only http://www.ncbi.nlm.nih.gov/pubmed/2837713).
Bennett et al. (2000) Pain 86:163-175.
Beyak et al. (2004) Am. J. Physiol. Gastrointest. Liver Physiol. 287:G845-G855.
Beyreuther (2004) "Pharmacology of SPM 927 and its relevance to clinical practice for neuropathic pain" Presented at Visiongain Pain Management, 2004.
Beyreuther et al. (2004) "SPM 927 displays potent antinociceptive effects in rat models for inflammatory and neuropathic pain" Poster presented at Neuropathic Pain, May 13-14, 2004.
Freynhagen et al. (2005) Pain 115:254-263.
Hama et al. (1999) Pharmacol. Biochem. Behavior 62:67-74.
Han et al. (2000) Pain 84:253-261.
Hao et al. (2004) "SPM 927, a new anti-epileptic drug, alleviates neuropathic pain-like behaviors in rats after spinal cord or trigeminal nerve injury" Poster presented at Neuropathic Pain—Changing Paradigms in Diagnosis and Treatment, Madrid, May 2004.
Hidvegi et al. (2006) "Lacosamide in subjects with painful distal diabetic neuropathy: results of a multi-center, open-label, follow-on trial" Poster presented at American Pain Society, May 3-6, 2006.
Hofmann et al. (2003) Eur. J. Pharmacol. 470:17-25.
Hong et al. (2004) J. Biol. Chem. 279(28):29341-29350.
Honore et al. (2000) Neurosci. 98(3):585-598.
Horstmann et al. (2002) Epilepsia 43(Suppl. 7):188, abst. 2.174.
Horstmann et al. (2003) Epilepsia 44(Suppl. 9):97, Abst. 1.271.
Horstmann et al. (2003) "SPM 927 does not prolong the QTc interval" Poster presented at 6th International Conference on the Mechanisms and Treatment of Neuropathic Pain, San Francisco, Sep. 18-20, 2003.
Hunt (2003) Clin. Orthopaedics Rel. Res. 409:96-105.
Hurley et al. (2002) Anesthesiology 97:1263-1273.
Ilyin et al. (2005) Br. J. Pharmacol. 144:801-812.
Jain (2000) Emerging Drugs 5(2):241-257.
Jensen (2000) Eur. J. Neurol. 7(Suppl. 3):3-4, abst. MT-9.
Kalso (2005) Curr. Pharm. Design 11:3005-3011.
Kenney et al. (2006) http://www.ampainsoc.org/db2/abstract/view?poster_id=2773#774.
Kim & Chung (1992) Pain 50(3):355-363.
Kropeit et al. (2004) Epilepsia 45(Suppl. 7): 123, abst. 1.323.
Lai et al. (2003) Curr. Opin. Neurobiol. 13:291-297.
Lai et al. (2004) Ann. Rev. Pharmacol. Toxicol. 44:371-397.
Lampert et al. (2006) Exp. Brain Res. 174(4):660-666.
Lawand et al. (1997) Eur. J. Pharmacol. 324:169-177.
Lee et al. (2000) NeuroReport 11(4):657-661.
Lesser et al. (2004) Neurology 63:2104-2110.
LeTiran et al. (2002) J. Med. Chem. 45:4762-4773.
Lockwood et al. (2002) N. Engl. J. Med. 347(12):904-910.
Lu & Westlund (1999) J. Pharmacol. Exp. Ther. 290:214-219.
Lynch et al. (2004) Pain 110:56-63.
Maier et al. (2004) "A pilot randomized, double-blind, placebo-controlled pilot trial to investigate safety and efficacy of SPM 927 in subjects with postherpetic neuralgia" Poster presented at Neuropathic Pain, May 13-14, 2004.
Majumdar et al. (2004) Eur. J. Neurosci. 20:127-143.
March (1985) Advance Organic Chemistry, New York: Wiley, pp. 16-18.
McCleane (2003) CNS Drugs 17(14):1031-1043.
McCleane et al. (2003) Neurosci. Lett. 352:117-120.
Moller (2000) J. Am. Acad. Audiol. 11(3):115-124.
Patel et al. (2001) Pain 90:217-226.
Priestley (2004) Curr. Drug Targets—CNS & Neurol. Disorders 3:441-456.
Rauck et al. (2003) "A randomized, double-blind, placebo-controlled trial to investigate the safety and efficacy of SPM 927 in painful diabetic neuropathy" Poster presented at 6th Int. Conf. on Mechanisms and Treatment of Neuropathic Pain, Sep. 2003.
Rauck et al. (2007) Clin. J. Pain 23(2):150-158.
Rauschkolb et al. (2004) "SPM 927, a novel promising pain treatment" Presented at Visiongain Pain Management, 2004.
Rodger (1991) Can. Med. Assoc. J. 145:1571-1581.
Rosenfeld et al. (2003) Epilepsia 44(Suppl. 9):262, abst. 2.249.
Rosenstock et al. (2004) Pain 110:628-638.
Schiltmeyer et al. (2004) Epilepsia 45(Suppl. 7):313, abst. 2.361.
Schiltmeyer et al. (2006) "No interaction between lacosamide and metformin" Poster 850 presented at American Pain Society 2006 (abstract at http://www.ampainsoc.org/db2/abstract/view?poster_id=2847#850).
Seltzer et al. (2001) Pain 93:101-106.
Shaibani et al. (2005) "An open-label follow-on trial to assess the long-term safety and efficacy of oral lacosamide in subjects with diabetic neuropathy" Poster presented at World Congress on Pain, Aug. 21-26, 2005.
Silver & Soderlund (2005) Neurotoxicol. 26:397-406.
Sindrup & Jensen (1999) Pain 83:389-400.
Sommerville (2003) "Schwarz Pharma's Neurology Pipeline" http://www.schwarzpharma.com/_uploads/assets/1369_4_neurology_KNS_190203.pdf.

Stoehr & Beyreuther (2005) "The effect of lacosamide in comparison to other analgesics in rat models for neuropathic pain" Poster presented at 8th Int. Conf. on Mechanisms and Treatment of Neuropathic Pain, San Francisco, Nov. 3-5, 2005.
Tahimic et al. (2006) Biochem. Biophys. Res. Comm. 340:1244-1250.
Teng & Abbott (1998) Pain 76:337-347.
Tjølsen & Hole (1997) in Dickinson & Besson, ed., "The Pharmacology of Pain", chap. 1, pp. 1-20; Berlin: Springer-Verlag.
Vos et al. (1994) J. Neurosci. 14(5):2708-2723.
Wood et al. (2002) in "Sodium Channels and Neuronal Hyperexcitability", pp. 159-172; Chichester: Wiley.
Wood et al. (2004) J. Neurobiol. 61:55-71.
Wymer et al. (2005) "A multi-center, randomized double-blind, placebo-controlled trial to assess the efficacy and safety of lacosamide in subjects with painful distal diabetic neuropathy." 8th Int. Conf. on Mechanisms and Treatment of Neuropathic Pain, San Francisco, Nov. 3-5, 2005.
Xu et al. (1992) Pain 48(2):279-290 (abstract only).
Yezierski et al. (1998) Pain 75:141-155.
Ziegler et al. (2005) "Efficacy and safety of lacosamide in the treatment of neuropathic pain attributed to distal diabetic neuropathy." 8th Int. Conf. on Mechanisms and Treatment of Neuropathic Pain, San Francisco, Nov. 3-5, 2005.
Beyreuther et al. (2006) "Effects of lacosamide as compared to other analgesics: a responder analysis in the streptozotocin rat model for diabetic neuropathic pain" Poster 618 presented at American Pain Society, 2006 (abstract at http://www.ampainsoc.org/db2/abstract/view?poster_id=2637#618).
Beyreuther et al. (2006) Eur. J. Pharmacol. 539:64-70.
Beyreuther et al. (2007) CNS Drug Rev. 13(1):21-42.
Beyreuther et al. (2007) Arthritis Res. Therapy 9:R14, http://arthritis-research.com/content/9/1/R14.
Bialer et al. (2002) Epilepsy Res. 51:31-71.
Biton et al. (2003) Epilepsia 44(Suppl. 9):259, abst. 2.241.
Blackburn-Munro et al. (2002) Eur. J. Pharmacol. 445:231-238.
Bretschneider et al. (2006) http://www.ampainsoc.org/db2/abstract/view?poster_id=2765#766.
Cawello et al. (2003) Epilepsia 44(Suppl. 9):95, abst. 1.265.
Cawello et al. (2004) Epilepsia 45(Suppl. 7):307, abst. 2.342.
Chevrier et al. (2004) Br. J. Pharmacol. 142:576-584.
Chipkin (2005) Am. J. Med. 118(5A):4S-13S.
Cummins et al. (2004) J. Neurosci. 24(38):8232-8236.
Decosterd & Woolf (2000) Pain 87:149-158.
Doty et al. (2004) in Bialer et al., Epilepsy Res. 61:1-48, pp. 14-16.
Doty et al. (2004) "Update on the clinical development of SPM 927 (formerly harkoseride)" Presented at EILAT VII, May 2004.
Dowdall et al. (2005) Pharmacol. Biochem. Behavior 80:93-108.
Dubuisson & Dennis (1977) Pain 4:161-174.
Duncan & Kohn (2005) Epilepsy Res. 67:81-87.
Eller et al. (2005) Neurosurg. Focus 18(5):E3, 3 pp.
Elliott (1997) Brain Res. 754:221-226.
Erichsen & Blackburn-Munro (2002) Pain 98:151-161.
Everill et al. (2001) Neurosci. 106(1):161-169.
Field et al. (1997) Br. J. Pharmacol. 121:1513-1522.
Field et al. (2002) J. Pharmacol. Exp. Ther. 303(2):730-735.
Macres (2000) "Understanding neuropathic pain" http://www.spineuniverse.com/displayarticle.php/article1614.html.
Morrow et al. (2001) Soc. Neurosci. Conf. Abst. 508.

Richeimer (2000) "The Richeimer Pain Update" http:/www.helpforpain.com/arch2000dec.htm.
Bennett et al. (1988) "A peripheral mononeuropathy in rat that produces disorders of pain sensation like those seen in man" Pain, 33:87-107.
Bennett et al. (1997) "Handbook of Experimental Pharmacology—The Pharmacology of Pain" 130:1-17.
Bialer et al. (2001) "Progress report on new antiepileptic drugs: a summary of the Fifth Eilat Conference (EILAT V)." Epilepsy Res. 43:11-58.
Bowsher (2007) "Chp. 6: Central Neuropathic Pain." Oxford Pain Management Library: Neuropathic Pain, Bennett, M., ed., New York: Oxford University Press.
Dawodu (2009) "Traumatic brain injury (TBI)—definition, epidemiology, pathophysiology." http://emedicine.medscape.com/article/326510-overview [retrieved on Nov. 25, 2009] pp. 1-11.
Finnerup et al., (2005) "Algorithm for neuropathic pain treatment: An evidence based proposal" 118:289-305.
Fisher, et al. (2003) "Trigeminal Neuralgia: current treatments and future developments." Expert Opin. Emerging Drugs 8(1):123-143.
Hans, et al. (2008) "Treatment of an acute severe central neuropathic pain syndrome by topical application of lidocaine 5% patch: a case report." Spinal Cord 46:311-313.
Hovinga (2002) "Novel anticonvulsant medications in development." Expert Opin. Investig. Drugs 11(10) 1387-1406.
Kim et al., (1993) "Effects of sympathectomy on a rat model of peripheral neuropathy" 55:85-92.
Klit et al. (2009) "Central post-stroke pain: clinical characteristics, pathophysiology, and management" 8:857-868.
Macres (2000) "Understanding neuropathic pain." www.spineuniverse.com/disiplayarticle.php/article1614._html (retrieved on Nov. 30, 2007) pp. 1-8.
Morrow et al. (2001) "Antinociceptive properties of the anticonvulsant SPM927 (harkoseride) in rat." Soc. Neurosci. Conf. Abst. 508.16.
Morrow et al. (2003) "The effects of SPM 927 in animal models for acute, inflammatory and neuropathic pain." Poster presented at AES Scientific Exhibit, Dec. 5-10, 2003.
Nash (2007) "Chp. 5: Peripheral neuropthic pain." Oxford Pain Management Library: Neuropathic Pain, Bennett, M., ed., New York: Oxford University Press.
Niespodziany et al. (2009) "Comparative study of lacosamide with classical sodium channel blocking antiepileptic drugs on sodium current slow inactivation." Poster presented at the American Epilepsy Society 63rd Annual Meeting as part of the UCB-Sponsored Scientific Exhibit, Dec. 6, 2009, Boston, MA.
"Pfizer's Lyrica approved in Europe for difficult-to-treat nerve pain." http://www.pharmpro.com/ShowPR.aspx?PUBCODE=021&ACCT=0000100&ISSUE=0... [retrieved on Nov. 25, 2009] pp. 1-2.
Uebachs, et al. (2009) "Effect of the new anticonvulsant drug lacosamide on persistent Na+-Current and firing behavior of hippocampal pyramidal cells." Poster presented at the American Epilepsy Society 63rd Annual Meeting as part of the UCB-Sponsored Scientific Exhibit, Dec. 6, 2009, Boston, MA.
Wang et al. (2003) "Animal and cellular models of chronic pain" 55:949-965.

* cited by examiner

METHOD FOR TREATING CENTRAL NEUROPATHIC PAIN

This application claims the benefit of the filing date of U.S. Provisional Application Ser. No. 60/530,895 filed Dec. 22, 2003.

The present invention is directed to the novel use of a class of peptide compounds for treating central neuropathic pain.

Certain peptides are known to exhibit central nervous system (CNS) activity and are useful in the treatment of epilepsy and other CNS disorders. These peptides which are described in the U.S. Pat. No. 5,378,729 have the Formula (Ia):

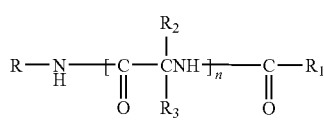

Formula (Ia)

wherein

R is hydrogen, lower alkyl, lower alkenyl, lower alkynyl, aryl, aryl lower alkyl, heterocyclic, heterocyclic lower alkyl, lower alkyl heterocyclic, lower cycloalkyl, lower cycloalkyl lower alkyl, and R is unsubstituted or is substituted with at least one electron withdrawing group or electron donating group;

$R_1$ is hydrogen or lower alkyl, lower alkenyl, lower alkynyl, aryl lower alkyl, aryl, heterocyclic lower alkyl, heterocyclic, lower cycloalkyl, lower cycloalkyl lower alkyl, each unsubstituted or substituted with an electron donating group or an electron withdrawing group; and $R_2$ and $R_3$ are independently hydrogen, lower alkyl, lower alkenyl, lower alkynyl, aryl lower alkyl, aryl, heterocyclic, heterocyclic lower alkyl, lower alkyl heterocyclic, lower cycloalkyl, lower cycloalkyl lower alkyl, or Z—Y wherein $R_2$ and $R_3$ may be unsubstituted or substituted with at least one electron withdrawing group or electron donating group;

Z is O, S, $S(O)_a$, $NR_4$, $PR_4$ or a chemical bond;

Y is hydrogen, lower alkyl, aryl, aryl lower alkyl, lower alkenyl, lower alkynyl, halo, heterocyclic, heterocyclic lower alkyl, and Y may be unsubstituted or substituted with an electron donating group or an electron withdrawing group, provided that when Y is halo, Z is a chemical bond, or ZY taken together is $NR_4NR_5R_7$, $NR_4OR_5$, $ONR_4R_7$, $OPR_4R_5$, $PR_4OR_5$, $SNR_4R_7$, $NR_4SR_7$, $SPR_4R_5$ or $PR_4SR_7$, $NR_4PR_5R_6$ or $PR_4NR_5R_7$,

$R_4$, $R_5$ and $R_6$ are independently hydrogen, lower alkyl, aryl, aryl lower alkyl, lower alkenyl, or lower alkynyl, wherein $R_4$, $R_5$ and $R_6$ may be unsubstituted or substituted with an electron withdrawing group or an electron donating group; and $R_7$ is $R_6$ or $COOR_8$ or $COR_8$;

$R_8$ is hydrogen or lower alkyl, or aryl lower alkyl, and the aryl or alkyl group may be unsubstituted or substituted with an electron withdrawing group or an electron donating group; and n is 1-4; and a is 1-3.

U.S. Pat. No. 5,773,475 also discloses additional compounds useful for treating CNS disorders. These compounds are N-benzyl-2-amino-3-methoxy-propionamide having the Formula (IIa):

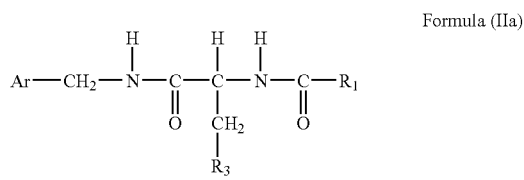

Formula (IIa)

wherein

Ar is aryl which is unsubstituted or substituted with halo; $R_3$ is lower alkoxy; and $R_1$ is methyl.

The patents U.S. Pat. No. 5,378,729 and U.S. Pat. No. 5,773,475 are hereby incorporated by reference. However, neither of these patents describes the use of these compounds as specific analgesics for the treatment of central neuropathic pain, especially spinal cord injury pain.

WO 02/074297 relates to the use of a compound according to Formula (IIa) wherein Ar is phenyl which may be substituted by at least one halo, $R_3$ is lower alkoxy containing 1-3 carbon atoms and $R_1$ is methyl for the preparation of pharmaceutical compositions useful for the treatment of allodynia related to peripheral neuropathic pain.

WO 02/074784 relates to the use of a compound having Formula (Ia) and/or Formula (IIa) showing antinociceptive properties for treating different types and symptoms of acute and chronic pain, especially non neuropathic inflammatory pain, e.g. rheumatoid arthritic pain and/or secondary inflammatory osteo-arthritic pain.

Pain is a subjective experience and the perception of pain is performed in particular parts of the Central Nervous System (CNS). Usually noxious (peripheral) stimuli are transmitted to the Central Nervous System (CNS) beforehand, but pain is not always associated with nociception. A broad variety of different types of clinical pain exists, that are derived from different underlying pathophysiological mechanisms and that will need different treatment approaches.

The perception of pain may be characterized by three major types of clinical pain:

acute pain chronic pain neuropathic pain

Acute clinical pain may result from inflammation or soft tissue injury, for instance. This type of pain is adaptive and has the biologically relevant function of warning and enabling healing and repair of an already damaged body part to occur undisturbed. A protective function is achieved by making the injured/inflamed area and surrounding tissue hypersensitive to all stimuli so that contact with any external stimulus is avoided. The neuronal mechanisms underlying this type of clinical pain are fairly well understood and pharmacological control of acute clinical pain is available and effective by means of e.g. Non-Steroidal Anti-inflammatory Drugs (NSAIDS) up to opioids depending on type and extension of the sensation.

Chronic clinical pain appears as sustained sensory abnormalities resulting from an ongoing peripheral pathology such as cancer or chronic inflammation (e.g. arthritis) or it can be independent of the initiating triggers. The latter being maladaptive, offering no survival advantage and very often no effective treatment is available.

There are several causes of human neuropathy with considerable variability in symptoms and neurological deficits. Painful neuropathies are defined as neurological disorders characterised by persistence of pain and hypersensitivity in a body region, of which the sensory innervation has been damaged, but damage to sensory nerves does not always produce neuropathic pain, usually loss of sensation rather than hypersensitivity or pain are observed.

Specific somatosensory disorders are referred to as allodynia (normally innocuous somatosensory stimulation evokes abnormal intense pain sensation with an explosive, radiating character often outlasting stimulus duration like a trigger), hyperalgesia (noxious stimulation evokes more intense and prolonged pain sensations), paresthesia (spontaneous aversive but nonpainful sensations, described as tingling or "pins and needles"), dysesthesia (evoked as well as spontaneous abnormal sensations).

Neuropathic pain can be classified as peripheral and central neuropathic pain. Peripheral neuropathic pain is caused by injury or infection of peripheral sensory nerves, whereas central neuropathic pain is caused by damage to the CNS and/or the spinal cord. Both peripheral and central neuropathic pain can occur without obvious initial nerve damage.

A similar definition is given by the International Association for the Study of Pain (IASP, Seattle, Wash., USA): peripheral neuropathic pain is pain initiated or caused by a primary lesion or dysfunction in the peripheral nervous system. Central neuropathic pain is pain initiated or caused by a primary lesion or dysfunction in the central nervous system.

Peripheral lesions may be lesions of perpherial nerves, e.g. diabetic neuropathy, drug-inducted neuropathy, e.g. upon chemotherapy, lesions of nerve roots and posterior gangli, e.g. post-herpetic neuralgia or nerve root avulsions, neuropathic cancer pain due to compression of peripheral nerves, nerve plexuses and nerve roots, etc. Central lesions may be lesions due to infarction, compressive tumors or abscesses e.g. in the thalamus or the brainstem, or due to Parkinson's disease, or may be spinal cord lesions due to injury or operations (Jain K K, Emerging Drugs, 2000, 5:241-257; McQuay, 2002, European Journal of Pain 6 (Suppl. A): 11-18).

The above examples of peripheral and central neuropathic pain demonstrate that peripheral and central neuropathic pain are distinguished not only by the anatomical location of the lesion or dysfunction, but they also demonstrate that peripheral and central neuropathic pain can be distinguished by its mechanisms (McQuay, supra). Consequently, there is no clear relation between drug action mechanism and the effect in distinct pain conditions or for single drug classes and different pain conditions (Sindrup S H, Jensen T S, Pain 1999, 83:389-400).

Common analgesics like opioids and non-steroidal anti-inflammatory drugs (NSAIDs) improve only insufficiently chronic abnormal pain syndromes as peripheral and central neuropathic pain due to insufficient efficacy or limiting side effects. In the search for alternative treatment regimes to produce satisfactory and sustained pain relief, corticosteroids, conduction blockade, glycerol, antidepressants, local anesthetics, gangliosides and electrostimulation have been tried, but mainly anti-convulsants have been found useful against various types of peripheral neuropathic pain conditions. A subset of patients with neuropathic pain responds to opioids.

Central neuropathic pain is a form of neuropathic pain which is a particularly difficult form to be treated (Yezierski and Burchiel, 2002). Due to lesions in the spinothalamocortical pathways, ectopic neuronal discharges can occur in different neurons of the spinal cord and brain. Hyperexcitability in damaged areas of the central nervous system plays a major role in the development of central neuropathic pain. Patients with central pain almost always have stimulus-independent pain. In the case of spinal cord injury, for example, stimulus-dependent pain may also be present, usually because skin areas or viscera below the lesions are allodynic. Thus, partial spinal lesions may tend to produce pain to a greater extent than do complete lesions.

Other accepted forms of central neuropathic pain or diseases associated with central neuropathic pain exist. Examples include inflammatory CNS diseases such as multiple sclerosis, myelitis or syphilis, ischemia, hemorrhages or asteriovenous malformations (e.g. post-stroke neuropathic pain) located in the thalamus, spinothalamic pathway or thalamocortical projections, and syrnigomyelia (Koltzenburg, Pain 2002—An Updated Review: Refresher Course Syllabus; IASP Press, Seattle, 2002).

The mechanisms of central neuropathic pain are poorly understood. Current treatments use a variety of pharmacological, surgical, physical and psychological approaches. However, the evidence for many of the treatments is still limited.

If general overactivity and unleaded low threshold activation of sensory neurons is considered as one of the main syndromes of neuropathy and neuropathic pain sensation with a marked mechanoallodynia as the most disabling clinical sympton, selective inhibition of this pathophysiological event instead of general inhibition of high threshold noxious stimuli (by e.g. local anesthetics) of the normal sensory nociception provides clear advantages.

Treatment of central neuropathic pain requires active substances having a different pharmacological profile to active substances useful for treatment of peripheral neuropathic pain due to different mechanisms and different location of the primary lesion or dysfunction in central and peripheral neuropathic pain. On the one hand, compounds which are employed in the treatment of peripherial neuropathic pain do not have any effect in central neuropathic pain, e.g. serotonin reuptake inhibitors (Sindrup and Jensen, supra). On the other hand, compounds which treat central neuropathic pain need to pass the blood-brain-barrier, a property which limits the number of compounds potentially useful for treatment of central neuropathic pain. It is concluded that there is still a need for new methods and new compounds for the prevention, alleviation or/and treatment of central neuropathic pain.

Animal models designed for distinguishing between central and neuropathic pain are reviewed e.g. by Tjølsen and Hole (1997, Handbook of Experimental Pharmacology, Vol. 130, The Pharmacology of Pain, A. Dickensen and J. M. Besson (eds.) Springer Verlag Berlin Heidelberg). These models are based on specific experimental lesions which are placed either in the central or in the peripheral nervous system of animals resulting in different pain syndromes as exemplified below.

A model of central neurophathic pain is the model of spinal cord injury in the rat described by Xu et al. (1992, Pain 48:279-290). In this model, an ischemic spinal cord injury is induced by laser irradiation for 5 to 20 min, resulting in an allodynia-like phenomenon lasting for several days, which is possibly related to dysfunction of the $GABAB_8$-system. In some animals, a chronic allodynia-like symptom lasting from 1 week to 1.5 months after injury, which is used as a model of chronic central pain. The allodynia seen in chronic spinally injured rats was similar to painful symptoms in patients after spinal cord injury or stroke.

A model of peripheral neuropathic pain is the neuroma model (Wall et al., 1979, Pain 7:103-113) of the denervated hindpaw of the rat by section of sciatic and saphenous nerves, leading to self-mutilation of the hindpaw on the side of nerve transsection, which behaviour is named "autotomy" and is interpreted as a response to spontaneous pain or dysesthesia.

Another model of peripheral neuropathic pain is the Bennett model (Bennett and Xie 1988, Pain 33:87-107, Bennett 1993, Muscle Nerve 16:1040-1048) in which a mononeuropathy is produced by placing four loosely constrictive ligatures around the common sciatic nerve. Upon this ligature, hyperalgesia develops in response to noxious heat stimuli, mustard oil and to mechanical stimuli. Injury-related discharge is discussed as a factor in the development of hyperalgesia in this model. Hovinga (Idrugs: The investigational drugs journal 2003, 6:479-485) and EP 1243 263 A1 describe the evaluation of the compound SPM 927 by the Bennett model.

The Chung model of peripheral neuropathic pain involves tight ligatures of spinal nerves in rats, either spinal nerves L5 or L5 and L6 (Kim and Chung, 1992, Pain 50:355-363) or in primates (L7). This model induces symptoms of neuropathy similar to those of the Bennett model. WO 02/15922 describes the evaluation of peptidic compounds by the Chung model.

In summary, there are fundamental differences in symptoms and the treatment of central and peripheral neuropathic pain. Therefore, no direct conclusion about beneficial effects in the treatment of central neuropathic pain can be drawn from data obtained in the models of peripheral neuropathic pain.

The use of compounds of Formula (Ib) or/and Formula (IIb) for treatment of central neuropathic pain has not been reported. Thus, the present invention concerns the use of said compounds of Formulae (Ib) or/and (IIb) for the preparation of a pharmaceutical composition for the treatment of all types of central neuropathic pain, especially, but not limited to, for the treatment of spinal cord injury pain.

Surprisingly, application of compounds (Ib) or/and (IIb), particularly (R)-2-acetamide-N-benzyl-3-methoxypropionamide (SPM 927) may produce a dose-dependent anti-allodynic effect in spinally injured rats, the well accepted animal model for central neuropathic pain, following single dose administration. Even more surprisingly, the chronic allodynia behaviour in test animals was found to be alleviated after long-term (e.g. for at least one week) administration without signs of tolerance development. The abolishment of allodynia following cessation of drug administration during chronic SPM 927 administration is particularly interesting since this has not been observed with other analgesics that have been tested in this model, including morphine (Yu et al. 1997a, b), gabapentin (Hao et al. 2000) and the adenosine analogue r-phenylisopropyladenosine (von Heijne et al. 1998). This is likely to be due to a cumulative effect from the repeated administration, resulting in normalization of basal sensitivity without signs of tolerance. Thus the compounds of the present invention, especially SPM 927, are suitable for the treatment for spinal cord injury pain in particular and centrally mediated neuropathic pain in general. Further, the compounds are suitable for reducing the susceptibility of patients to spinal cord injury pain in particular and centrally mediated neuropathic pain in general. The invention is applicable for human or veterinary medicine.

Thus, a compound according to the invention useful for the treatment of central neuropathic pain, preferably for treatment of spinal cord injury pain, has the general Formula (Ib)

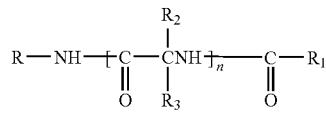

Formula (Ib)

wherein

R is hydrogen, lower alkyl, lower alkenyl, lower alkynyl, aryl, aryl lower alkyl, heterocyclic, heterocyclic lower alkyl, lower alkyl heterocyclic, lower cycloalkyl or lower cycloalkyl lower alkyl, and R is unsubstituted or is substituted with at least one electron withdrawing group, or/and electron donating group;

$R_1$ is hydrogen or lower alkyl, lower alkenyl, lower alkynyl, aryl lower alkyl, aryl, heterocyclic lower alkyl, lower alkyl heterocyclic, heterocyclic, lower cycloalkyl, lower cycloalkyl lower alkyl, each unsubstituted or substituted with an electron donating group or/and an electron withdrawing group; and $R_2$ and $R_3$ are independently hydrogen, lower alkyl, lower alkenyl, lower alkynyl, aryl lower alkyl, aryl, halo, heterocyclic, heterocyclic lower alkyl, lower alkyl heterocyclic, lower cycloalkyl, lower cycloalkyl lower alkyl, or Z—Y wherein $R_2$ and $R_3$ may be unsubstituted or substituted with at least one electron withdrawing group or/and electron donating group;

Z is O, S, S(O)$_a$, $NR_4$, $NR_{16}$, $PR_4$ or a chemical bond;

Y is hydrogen, lower alkyl, aryl, aryl lower alkyl, lower alkenyl, lower alkynyl, halo, heterocyclic, heterocyclic lower alkyl, lower alkyl heterocyclic and Y may be unsubstituted or substituted with an electron donating group or/and an electron withdrawing group, provided that when Y is halo, Z is a chemical bond, or ZY taken together is $NR_4NR_5R_7$, $NR_4OR_5$, $ONR_4R_7$, $OPR_4R_5$, $PR_4OR_5$, $SNR_4R_7$, $NR_4SR_7$, $SPR_4R_5$, $PR_4SR_7$, $NR_4PR_5R_6$, $PR_4NR_5R_7$ or $N+R_5R_6R_7$,

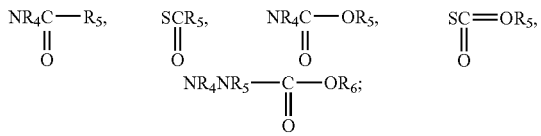

$R'_6$ is hydrogen, lower alkyl, lower alkenyl, or lower alkenyl which may be unsubstituted or substituted with an electron withdrawing group or/and electron donating group;

$R_4$, $R_5$ and $R_6$ are independently hydrogen, lower alkyl, aryl, aryl lower alkyl, lower alkenyl, or lower alkynyl, wherein $R_4$, $R_5$ and $R_6$ may independently be unsubstituted or substituted with an electron withdrawing group or/and an electron donating group;

$R_7$ is $R_6$ or $COOR_8$ or $COR_8$, which $R_7$ may be unsubstituted or substituted with an electron withdrawing group or/and an electron donating group;

$R_8$ is hydrogen or lower alkyl, or aryl lower alkyl, and the aryl or alkyl group may be unsubstituted or substituted with an electron withdrawing group or/and an electron donating group; and n is 1-4; and a is 1-3.

Furthermore a compound according to the invention has the general Formula (IIb)

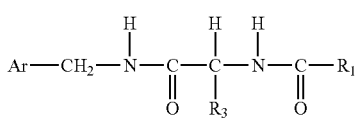

Formula (IIb)

wherein

Ar is aryl, especially phenyl, which is unsubstituted or substituted with at least one halo; $R_3$ is —$CH_2$-Q, wherein Q is lower alkoxy; and $R_1$ is lower alkyl, especially methyl.

The present invention is also directed to the preparation of pharmaceutical compositions comprising a compound according to Formula (Ib) and/or Formula (IIb) useful for the treatment of central neuropathic pain, preferably spinal cord injury pain.

Further, the present invention is directed to a pharmaceutical composition comprising a compound according to Formula (Ib) and/or Formula (IIb) for the treatment of central neuropathic pain, preferably spinal cord injury pain.

The compounds of Formula (Ia) are described in U.S. Pat. No. 5,378,729, the contents of which are incorporated by reference.

The "lower alkyl" groups when used alone or in combination with other groups, are lower alkyl containing from 1 to 6 carbon atoms, especially 1 to 3 carbon atoms, and may be straight chain or branched. These groups include methyl, ethyl, propyl, isopropyl, butyl, isobutyl, tertiary butyl, amyl, hexyl, and the like.

The "lower alkoxy" groups are lower alkoxy containing from 1 to 6 carbon atoms, especially 1 to 3 carbon atoms, and may be straight chain or branched. These groups include methoxy, ethoxy, propoxy, butoxy, isobutoxy, tert-butoxy, pentoxy, hexoxy and the like.

The "aryl lower alkyl" groups include, for example, benzyl, phenethyl, phenpropyl, phenisopropyl, phenbutyl, diphenylmethyl, 1,1-diphenylethyl, 1,2-diphenylethyl, and the like.

The term "aryl", when used alone or in combination, refers to an aromatic group which contains from 6 up to 18 ring carbon atoms and up to a total of 25 carbon atoms and includes the polynuclear aromatics. These aryl groups may be monocyclic, bicyclic, tricyclic or polycyclic and are fused rings. A polynuclear aromatic compound as used herein, is meant to encompass bicyclic and tricyclic fused aromatic ring systems containing from 10-18 ring carbon atoms and up to a total of 25 carbon atoms. The aryl group includes phenyl, and the polynuclear aromatics e.g., naphthyl, anthracenyl, phenanthrenyl, azulenyl and the like. The aryl group also includes groups like ferrocyenyl.

"Lower alkenyl" is an alkenyl group containing from 2 to 6 carbon atoms and at least one double bond. These groups may be straight chained or branched and may be in the Z or E form. Such groups include vinyl, propenyl, 1-butenyl, isobutenyl, 2-butenyl, 1-pentenyl, (Z)-2-pentenyl, (E)-2-pentenyl, (Z)-4-methyl-2-pentenyl, (E)-4-methyl-2-pentenyl, pentadienyl, e.g., 1, 3 or 2,4-pentadienyl, and the like.

The term "lower alkynyl" is an alkynyl group containing 2 to 6 carbon atoms and may be straight chained as well as branched. It includes such groups as ethynyl, propynyl, 1-butynyl, 2-butynyl, 1-pentynyl, 2-pentynyl, 3-methyl-1-pentynyl, 3-pentynyl, 1-hexynyl, 2-hexynyl, 3-hexynyl and the like.

The term "lower cycloalkyl" when used alone or in combination is a cycloalkyl group containing from 3 to 18 ring carbon atoms and up to a total of 25 carbon atoms. The cycloalkyl groups may be monocyclic, bicyclic, tricyclic, or polycyclic and the rings are fused. The cycloalkyl may be completely saturated or partially saturated. Examples include cyclopropyl, cyclobutyl, cyclopentyl, cyclohexyl, cycloheptyl, cyclooctyl, cyclodecyl, cyclohexenyl, cyclopentenyl, cyclooctenyl, cycloheptenyl, decalinyl, hydroindanyl, indanyl, fenchyl, pinenyl, adamantyl, and the like. Cycloalkyl includes the cis or trans forms. Cycloalkyl groups may be unsubstituted or mono or polysubstituted with electron withdrawing or/and electron donating groups as described below. Furthermore, the substituents may either be in endo or exo positions in the bridged bicyclic systems.

The term "electron-withdrawing and electron donating" refer to the ability of a substituent to withdraw or donate electrons, respectively, relative to that of hydrogen if the hydrogen atom occupied the same position in the molecule. These terms are well understood by one skilled in the art and are discussed in Advanced Organic Chemistry, by J. March, John Wiley and Sons, New York, N.Y., pp. 16-18 (1985) and the discussion therein is incorporated herein by reference. Electron withdrawing groups include halo, including bromo, fluoro, chloro, iodo and the like; nitro, carboxy, lower alkenyl, lower alkynyl, formyl, carboxyamido, aryl, quaternary ammonium, haloalkyl such as trifluoromethyl, aryl lower alkanoyl, carbalkoxy and the like. Electron donating groups include such groups as hydroxy, lower alkoxy, including methoxy, ethoxy and the like; lower alkyl, such as methyl, ethyl, and the like; amino, lower alkylamino, di(loweralkyl)amino, aryloxy such as phenoxy, mercapto, lower alkylthio, lower alkylmercapto, disulfide (lower alkyldithio) and the like. One of ordinary skill in the art will appreciate that some of the aforesaid substituents may be considered to be electron donating or electron withdrawing under different chemical conditions. Moreover, the present invention contemplates any combination of substituents selected from the above-identified groups.

The term "halo" includes fluoro, chloro, bromo, iodo and the like.

The term "acyl" includes lower alkanoyl containing from 1 to 6 carbon atoms and may be straight chains or branched. These groups include, for example, formyl, acetyl, propionyl, butyryl, isobutyryl, tertiary butyryl, pentanoyl and hexanoyl.

As employed herein, the heterocyclic substituent contains at least one sulfur, nitrogen or oxygen ring atom, but also may include one or several of said atoms in the ring. The heterocyclic substituents contemplated by the present invention include heteroaromatics and saturated and partially saturated heterocyclic compounds. These heterocyclics may be monocyclic, bicyclic, tricyclic or polycyclic and are fused rings. They may contain up to 18 ring atoms and up to a total of 17 ring carbon atoms and a total of up to 25 carbon atoms. The heterocyclics are also intended to include the so-called benzoheterocyclics. Representative heterocyclics include furyl, thienyl, pyrazolyl, pyrrolyl, methylpyrrolyl, imidazolyl, indolyl, thiazolyl, oxazolyl, isothiazolyl, isoxazolyl, piperidyl, pyrrolinyl, piperazinyl, quinolyl, triazolyl, tetrazolyl, isoquinolyl, benzofuryl, benzothienyl, morpholinyl, benzoxazolyl, tetrahydrofuryl, pyranyl, indazolyl, purinyl, indolinyl, pyrazolindinyl, imidazolinyl, imadazolindinyl, pyrrolidinyl, furazanyl, N-methylindolyl, methylfuryl, pyridazinyl, pyrimidinyl, pyrazinyl, pyridyl, epoxy, aziridino, oxetanyl, azetidinyl, the N-oxides of the nitrogen containing heterocycles, such as the N-oxides of pyridyl, pyrazinyl, and pyrimidinyl and the like. Heterocyclic groups may be unsubstituted or mono or polysubstituted with electron withdrawing or/and electron donating groups.

The preferred heterocyclics are thienyl, furyl, pyrrolyl, benzofuryl, benzothienyl, indolyl, methylpyrrolyl, morpholinyl, pyridiyl, pyrazinyl, imidazolyl, pyrimidinyl, or pyridazinyl. The preferred heterocyclic is a 5 or 6-membered heterocyclic compound. The especially preferred heterocyclic is furyl, pyridyl, pyrazinyl, imidazolyl, pyrimidinyl, or pyridazinyl. The most preferred heterocyclics are furyl and pyridyl.

The preferred compounds are those wherein n is 1, but di (n=2), tri (n=3) and tetrapeptides (n=4) are also contemplated to be within the scope of the invention.

The preferred values of R is aryl lower alkyl, especially benzyl especially those wherein the phenyl ring thereof is unsubstituted or substituted with electron donating groups or electron withdrawing groups, such as halo (e.g., F).

The preferred $R_1$ is H or lower alkyl. The most preferred $R_1$ group is methyl.

The preferred electron donating substituents or/and electron withdrawing substituents are halo, nitro, alkanoyl, formyl, arylalkanoyl, aryloyl, carboxyl, carbalkoxy, carboxamido, cyano, sulfonyl, sulfoxide, heterocyclic, guanidine, quaternary ammonium, lower alkenyl, lower alkynyl, sulfonium salts, hydroxy, lower alkoxy, lower alkyl, amino, lower alkylamino, di(loweralkyl) amino, amino lower alkyl, mercapto, mercaptoalkyl, alkylthio, and alkyldithio. The term "sulfide" encompasses mercapto, mercapto alkyl and alkylthio, while the term disulfide encompasses alkyldithio. Especially preferred electron donating or/and electron withdrawing groups are halo or lower alkoxy, most preferred are fluoro or methoxy. These preferred substituents may be substituted on any one of R, $R_1$, $R_2$, $R_3$, $R_4$, $R_5R_6$, $R'_6$, $R_7$, $R_8$ or/and $R_{50}$ as defined herein.

The ZY groups representative of $R_2$ and $R_3$ include hydroxy, alkoxy, such as methoxy, ethoxy, aryloxy, such as phenoxy; thioalkoxy, such as thiomethoxy, thioethoxy; thioaryloxy such as thiophenoxy; amino; alkylamino, such as methylamino, ethylamino; arylamino, such as anilino; lower dialkylamino, such as, dimethylamino; trialkyl ammonium salt, hydrazino; alkylhydrazino and arylhydrazino, such as N-methylhydrazino, N-phenylhydrazino, carbalkoxy hydrazino, aralkoxycarbonyl hydrazino, aryloxycarbonyl hydrazino, hydroxylamino, such as N-hydroxylamino (—NH—OH), lower alkoxy amino [(NHOR$_{18}$) wherein $R_{18}$ is lower alkyl], N-lower alkylhydroxylamino [(NR$_{18}$)OH wherein $R_{18}$ is lower alkyl], N-lower alkyl-O-lower alkylhydroxyamino, i.e., [N(R$_{18}$)OR$_{19}$ wherein $R_{18}$ and $R_{19}$ are independently lower alkyl], and o-hydroxylamino (—O—NH$_2$); alkylamido such as acetamido; trifluoroacetamido; lower alkoxyamino, (e.g., NH(OCH$_3$)); and heterocyclicamino, such as pyrazoylamino.

The preferred heterocyclic groups representative of $R_2$ and $R_3$ are monocyclic 5- or 6-membered heterocyclic moieties of the formula:

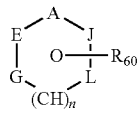

or those corresponding partially or fully saturated form thereof wherein n is 0 or 1; and $R_{50}$ is H or an electron withdrawing group or electron donating group;

A, E, L, J and G are independently CH, or a heteroatom selected from the group consisting of N, O, S;

but when n is 0, G is CH, or a heteroatom selected from the group consisting of NH, O and S with the proviso that at most two of A, E, L, J and G are heteroatoms.

When n is 0, the above heteroaromatic moiety is a five membered ring, while if n is 1, the heterocyclic moiety is a six membered monocyclic heterocyclic moiety. The preferred heterocyclic moieties are those aforementioned heterocyclics which are monocyclic.

If the ring depicted hereinabove contains a nitrogen ring atom, then the N-oxide forms are also contemplated to be within the scope of the invention.

When $R_2$ or $R_3$ is a heterocyclic of the above formula, it may be bonded to the main chain by a ring carbon atom. When n is 0, $R_2$ or $R_3$ may additionally be bonded to the main chain by a nitrogen ring atom.

Other preferred moieties of $R_2$ and $R_3$ are hydrogen, aryl, e.g., phenyl, aryl alkyl, e.g., benzyl and alkyl.

It is to be understood that the preferred groups of $R_2$ and $R_3$ may be unsubstituted or substituted with electron donating or/and electron withdrawing groups. It is preferred that $R_2$ and $R_3$ are independently hydrogen, lower alkyl, which is either unsubstituted or substituted with an electron withdrawing group or/and an electron donating group, such as lower alkoxy (e.g., methoxy, ethoxy, and the like), N-hydroxylamino, N-lower alkylhydroxyamino, N-loweralkyl-O-loweralkyl and alkylhydroxyamino.

It is preferred that one of $R_2$ and $R_3$ is hydrogen.

It is preferred that n is one.

It is more prefered that n=1 and one of $R_2$ and $R_3$ is hydrogen. It is especially preferred that in this embodiment, $R_2$ is hydrogen and $R_3$ is lower alkyl or ZY;

Z is O, NR$_4$ or PR$_4$; Y is hydrogen or lower alkyl; ZY is NR$_4$NR$_5$R$_7$, NR$_4$OR$_5$, ONR$_4$R$_7$,

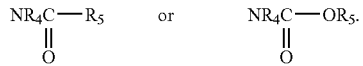

In another especially preferred embodiment, n=1, $R_2$ is hydrogen and $R_3$ is lower alkyl which may be substituted or unsubstituted with an electron donating or electron withdrawing group, NR$_4$OR$_5$, or ONR$_4$R$_7$.

In yet another especially preferred embodiment, n=1, $R_2$ is hydrogen and $R_3$ is lower alkyl which is unsubstituted or substituted with hydroxy or loweralkoxy, NR$_4$OR$_5$ or ONR$_4$R$_7$, wherein $R_4$, $R_5$ and $R_7$ are independently hydrogen or lower alkyl, R is aryl lower alkyl, which aryl group may be unsubstituted or substituted with an electron withdrawing group and $R_1$ is lower alkyl. In this embodiment it is most preferred that aryl is phenyl, which is unsubstituted or substituted with halo.

It is preferred that $R_2$ is hydrogen and $R_3$ is hydrogen, an alkyl group which is unsubstituted or substituted by at least an electron donating or electron withdrawing group or ZY. In this preferred embodiment, it is more preferred that $R_3$ is hydrogen, an alkyl group such as methyl, which is unsubstituted or substituted by an electron donating group, or NR$_4$OR$_5$ or ONR$_4$R$_7$, wherein $R_4$, $R_5$ and $R_7$ are independently hydrogen or lower alkyl. It is preferred that the electron donating group is lower alkoxy, and especially methoxy or ethoxy.

It is preferred that $R_2$ and $R_3$ are independently hydrogen, lower alkyl, or ZY;

Z is O, NR$_4$ or PR$_4$;

Y is hydrogen or lower alkyl or

ZY is NR$_4$R$_5$R$_7$, NR$_4$OR$_5$, ONR$_4$R$_7$,

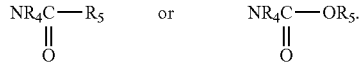

It is also preferred that R is aryl lower alkyl. The most preferred aryl for R is phenyl. The most preferred R group is benzyl. In a preferred embodiment, the aryl group may be unsubstituted or substituted with an electron donating or electron withdrawing group. If the aryl ring in R is substituted, it is most preferred that it is substituted with an electron withdrawing group, especially on the aryl ring. The most preferred electron withdrawing group for R is halo, especially fluoro.

The preferred $R_1$ is lower alkyl, especially methyl.

It is more preferred that R is aryl lower alkyl and $R_1$ is lower alkyl.

Further preferred compounds are compounds of Formula (Ib) wherein n is 1; $R_2$ is hydrogen; $R_3$ is hydrogen, a lower alkyl group, especially methyl which is substituted by an electron donating or electron withdrawing group or ZY; R is aryl, aryl lower alkyl, such as benzyl, wherein the aryl group is unsubstituted or substituted with an electron donating or electron withdrawing group and $R_1$ is lower alkyl. In this embodiment, it is more preferred that $R_3$ is hydrogen, a lower alkyl group, especially methyl, which may be substituted by electron donating group, such as lower alkoxy, (e.g., methoxy, ethoxy and the like), $NR_4OR_5$ or $ONR_4R_7$ wherein these groups are defined hereinabove.

The most preferred compounds utilized are those of the Formula (IIb):

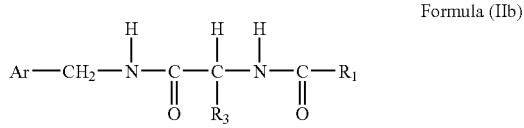

Formula (IIb)

wherein
Ar is aryl, especially phenyl, which is unsubstituted or substituted with at least one electron donating group or electron withdrawing group, especially halo,
$R_1$ is lower alkyl, especially containing 1-3 carbon atoms; and
$R_3$ is as defined herein, but especially hydrogen, loweralkyl, which is unsubstituted or substituted by at least an electron donating group or electron withdrawing group or ZY. It is even more preferred that $R_3$ is, in this embodiment, hydrogen, an alkyl group which is unsubstituted or substituted by an electron donating group, $NR_4OR$ or $ONR_4R_7$. It is most preferred that $R_3$ is $CH_2$-Q, wherein Q is lower alkoxy, especially containing 1-3 carbon atoms; $NR_4OR_5$ or $ONR_4R_7$ wherein $R_4$ is hydrogen or alkyl containing 1-3 carbon atoms, $R_5$ is hydrogen or alkyl containing 1-3 carbon atoms, and $R_7$ is hydrogen or alkyl containing 1-3 carbon atoms.

The most preferred $R_1$ is $CH_3$. The most preferred $R_3$ is $CH_2$-Q, wherein Q is methoxy.

The most preferred aryl is phenyl. The most preferred halo is fluoro.

The most preferred compound includes:
(R)-2-acetamido-N-benzyl-3-methoxy-propionamide,
O-methyl-N-acetyl-D-serine-m-fluorobenzyl-amide;
O-methyl-N-acetyl-D-serine-p-fluorobenzyl-amide;
N-acetyl-D-phenylglycine benzylamide;
D-1,2-(N,O-dimethylhydroxylamino)-2-acetamide acetic acid benzylamide;
D-1,2-(O-methylhydroxylamino)-2-acetamido acetic acid benzylamide.

It is to be understood that the various combinations and permutations of the Markush groups of $R_1$, $R_2$, $R_3$, R and n described herein are contemplated to be within the scope of the present invention. Moreover, the present invention also encompasses compounds and compositions which contain one or more elements of each of the Markush groupings in $R_1$, $R_2$, $R_3$, n and R and the various combinations thereof. Thus, for example, the present invention contemplates that $R_1$ may be one or more of the substituents listed hereinabove in combination with any and all of the substituents of $R_2$, $R_3$, and R with respect to each value of n.

The compounds utilized in the present invention may contain one or more asymmetric carbons and may exist in racemic and optically active forms. The configuration around each asymmetric carbon can be either the D or L form. It is well known in the art that the configuration around a chiral carbon atoms can also be described as R or S in the Cahn-Prelog-Ingold nomenclature system. All of the various configurations around each asymmetric carbon, including the various enantiomers and diastereomers as well as racemic mixtures and mixtures of enantiomers, diastereomers or both are contemplated by the present invention.

In the principal chain, there exists asymmetry at the carbon atom to which the groups $R_2$ and $R_3$ are attached. When n is 1, the compounds of the present invention is of the formula

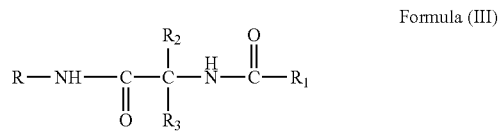

Formula (III)

wherein R, $R_1$, $R_2$, $R_3$, $R_4$, $R_5$, $R_6$, $R'_6$, $R_7$, $R_8$, $R_{50}$ Z and Y are as defined previously.

As used herein, the term configuration shall refer to the configuration around the carbon atom to which $R_2$ and $R_3$ are attached, even though other chiral centers may be present in the molecule. Therefore, when referring to a particular configuration, such as D or L, it is to be understood to mean the D or L stereoisomer at the carbon atom to which $R_2$ and $R_3$ are attached. However, it also includes all possible enantiomers and diastereomers at other chiral centers, if any, present in the compound.

The compounds of the present invention are directed to all the optical isomers, i.e., the compounds of the present invention are either the L-stereoisomer or the D-stereoisomer (at the carbon atom to which $R_2$ and $R_3$ are attached). These stereoisomers may be found in mixtures of the L and D stereoisomer, e.g., racemic mixtures. The D stereoisomer is preferred.

It is also preferred that the compounds of the present invention be substantially enantiomerically pure, i.e., substantially free from the corresponding S isomer. It is more preferred that the compounds of the present invention contain at least 90% (w/w) R stereoisomer, and most preferably greater than about 95% (w/w) in the R stereoisomer. Thus, the present invention contemplates compounds having at most about 10% S isomer (w/w), and even more preferably less than about 5% S isomer (w/w).

More preferred is a compound of Formula (III) in the R configuration, preferably substantially enantiopure, wherein the substituent R is benzyl which is unsubstituted or substituted with at least one halo group, wherein $R_3$ is $CH_2$-Q, wherein Q is lower alkoxy containing 1-3 carbon atoms and wherein $R_1$ is methyl. Preferably R is unsubstituted benzyl or benzyl substituted with at least one halo group which is a fluoro group.

Depending upon the substituents, the present compounds may form addition salts as well. All of these forms are contemplated to be within the scope of this invention including mixtures of the stereoisomeric forms.

The preparation of the utilized compounds are described in U.S. Pat. Nos. 5,378,729 and 5,773.475, the contents of both of which are incorporated by reference.

The compounds utilized in the present invention are useful as such as depicted in the Formulae (Ib) or/and (IIb) can be employed in the form of salts in view of its basic nature by the presence of the free amino group. Thus, the compounds of Formulae (Ib) or/and (IIb) form salts with a wide variety of acids, inorganic and organic, including pharmaceutically acceptable acids. The salts with therapeutically acceptable acids are of course useful in the preparation of formulation where enhanced water solubility is most advantageous.

These pharmaceutically acceptable salts have also therapeutic efficacy. These salts include salts of inorganic acids such as hydrochloric, hydroiodic, hydrobromic, phosphoric, metaphosphoric, nitric acid and sulfuric acids as well as salts of organic acids, such as tartaric, acetic, citric, malic, benzoic, perchloric, glycolic, gluconic, succinic, aryl sulfonic, (e.g., p-toluene sulfonic acids, benzenesulfonic), phosphoric, malonic, and the like.

The present invention is further directed to a method for the prevention, alleviation or/and treatment of a disease or condition as described above in a mammal, including a human being, comprising administering at least one compound of Formulae (Ib) or/and (IIb).

It is preferred that the compound utilized in the present invention is used in therapeutically effective amounts.

The physician will determine the dosage of the present therapeutic agents which will be most suitable and it will vary with the form of administration and the particular compound chosen, and furthermore, it will vary with the patient under treatment, the age of the patient, the type of malady being treated. He will generally wish to initiate treatment with small dosages substantially less than the optimum dose of the compound and increase the dosage by small increments until the optimum effect under the circumstances is reached. When the composition is administered orally, larger quantities of the active agent will be required to produce the same effect as a smaller quantity given parenterally. The compounds are useful in the same manner as comparable therapeutic agents and the dosage level is of the same order of magnitude as is generally employed with these other therapeutic agents.

In a preferred embodiment, the compounds utilized are administered in amounts ranging from about 1 mg to about 100 mg per kilogram of body weight per day. This dosage regimen may be adjusted by the physician to provide the optimum therapeutic response.

Patients in need thereof may be treated with doses of the compound of the present invention of at least 50 mg/day, preferably of at least 200 mg/day, more preferably of at least 300 mg/day and most preferably of at least 400 mg/day. Generally, a patient in need thereof may be treated with doses at a maximum of 6 g/day, more preferably a maximum of 1 g/day and most preferably a maximum of 600 mg/day. In some cases, however, higher or lower doses may be needed.

In another preferred embodiment, the daily doses are increased until a predetermined daily dose is reached which is maintained during the further treatment.

In yet another preferred embodiment, several divided doses may be administered daily or the dose may be proportionally reduced as indicated by the exigencies of the therapeutic situation. For example, three doses per day may be administered, preferably two doses per day. It is more preferred to administer a single dose per day.

In yet another preferred embodiment, an amount of the compounds of the present invention may be administered which results in a plasma concentration of 0.1 to 15 µg/ml (trough) and 5 to 18.5 µg/ml (peak), calculated as an average over a plurality of treated subjects.

The compounds of Formulae (Ib) or/and (IIb) may be administered in a convenient manner, such as by oral, intravenous (where water soluble), intramuscular, intrathecal or subcutaneous routes. Oral or/and i.v. administration is preferred.

The pharmaceutical composition of the present invention may be prepared for the treatment regimen as described above, in particular for the treatment with doses as described above, to effect plasma concentrations as described above, for administration periods or/and administration routes as specified in the embodiments of the present invention as described above.

In another preferred embodiment, the method of the present invention as described above for the treatment of a mammal including a human being in need thereof comprises administering a compound of the present invention in combination with administering a further active agent for the prevention, alleviation or/and treatment of central neuropathic pain. The compound of the present invention and the further active agent may be administered together, i.e. in a single dose form, or may be administered separately, i.e. in a separate dose form. Thus, the pharmaceutical composition of the present invention may comprise a compound of the present invention as defined above and may further comprise a further active agent for the prevention, alleviation or/and treatment of central neuropathic pain. The pharmaceutical composition may comprise a single dose form or may comprise a separate dose form comprising a first composition comprising a compound of the present invention as defined above and a second composition comprising the further active agent.

The compounds of Formulae (Ib) or/and (IIb) may be orally administered, for example, with an inert diluent or with an assimilable edible carrier, or it may be enclosed in hard or soft shell gelatin capsules, or it may be compressed into tablets, or it may be incorporated directly into the fool of the diet. For oral therapeutic administration, the active compound of Formulae (Ib) or/and (IIb) may be incorporated with excipients and used in the form of ingestible tablets, buccal tablets, troches, capsules, elixirs, suspensions, syrups, wafers, and the like. Such compositions and preparations should contain at least 1% of active compound of Formulae (Ib) or/and (IIb). The percentage of the compositions and preparations may, of course, be varied and may conveniently be between about 5 to about 80% of the weight of the unit. The amount of active compound of Formulae (Ib) or/and (IIb) in such therapeutically useful compositions is such that a suitable dosage will be obtained. Preferred compositions or preparations according to the present invention contains between about 10 mg and 6 g active compound of Formulae (Ib) or/and (IIb).

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier.

Various other materials may be present as coatings or otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations. For example, sustained release dosage forms are contemplated wherein the active ingredient is bound to an ion exchange resin which, optionally, can be coated with a diffusion barrier coating to modify the release properties of the resin.

The active compound may also be administered parenterally or intraperitoneally. Dispersions can also be prepared in glycerol, liquid, polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying the freeze-drying technique plus any additional desired ingredient from previously sterile-filtered solution thereof.

As used herein, "pharmaceutically acceptable carrier" includes any and all solvents, dispersion media, coatings, antibacterial and antifungal agent, isotonic and absorption delaying agents for pharmaceutical active substances as well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form or ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specifics for the novel dosage unit forms of the invention are dictated by and directly dependent on (a) the unique characteristics of the active material an the particular therapeutic effect to be achieved, and (b) the limitations inherent in the art of compounding such as active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore described. A unit dosage form can, for example, contain the principal active compound in amounts ranging from about 10 mg to about 6 g. Expressed in proportions, the active compound is generally present in from about 1 to about 750 mg/ml of carrier. In the case of compositions containing supplementary active ingredients, the dosages are determined by reference to the usual dose and manner of administration of the said ingredients.

As used herein the term "patient" or "subject" refers to a warm blooded animal, and preferably mammals, such as, for example, cats, dogs, horses, cows, pigs, mice, rats and primates, including humans. The preferred patient is humans.

The term "treat" refers to either relieving the pain associated with a disease or condition or alleviating the patient's disease or condition.

The compounds of the present invention are administered to a patient suffering from the aforementioned type of pain in an analgesic effective amount. These amounts are equivalent to the therapeutically effective amounts described hereinabove.

The following working example shows the properties in a well-defined animal model of central neuropathic pain, in particular spinal cord injury pain.

The used substance was SPM 927 which is the synonym for Harkoseride. The standard chemical nomenclature is (R)-2-acetamide-N-benzyl-3-methoxypropionamide.

FIGURE LEGEND

FIG. 1 shows the effect of vehicle (open circles), SPM 927 at 10 (open squares), 15 (filled circles) and 20 mg/kg (filled squares) on vocalization threshold to stimulation with von Frey hairs (A), brushing (B) and cold (C) in spinally injured rates. *=p<0.05 compared to baseline at time 0 with Wilcoxon signed-ranks test (A-C).

Figure 2:
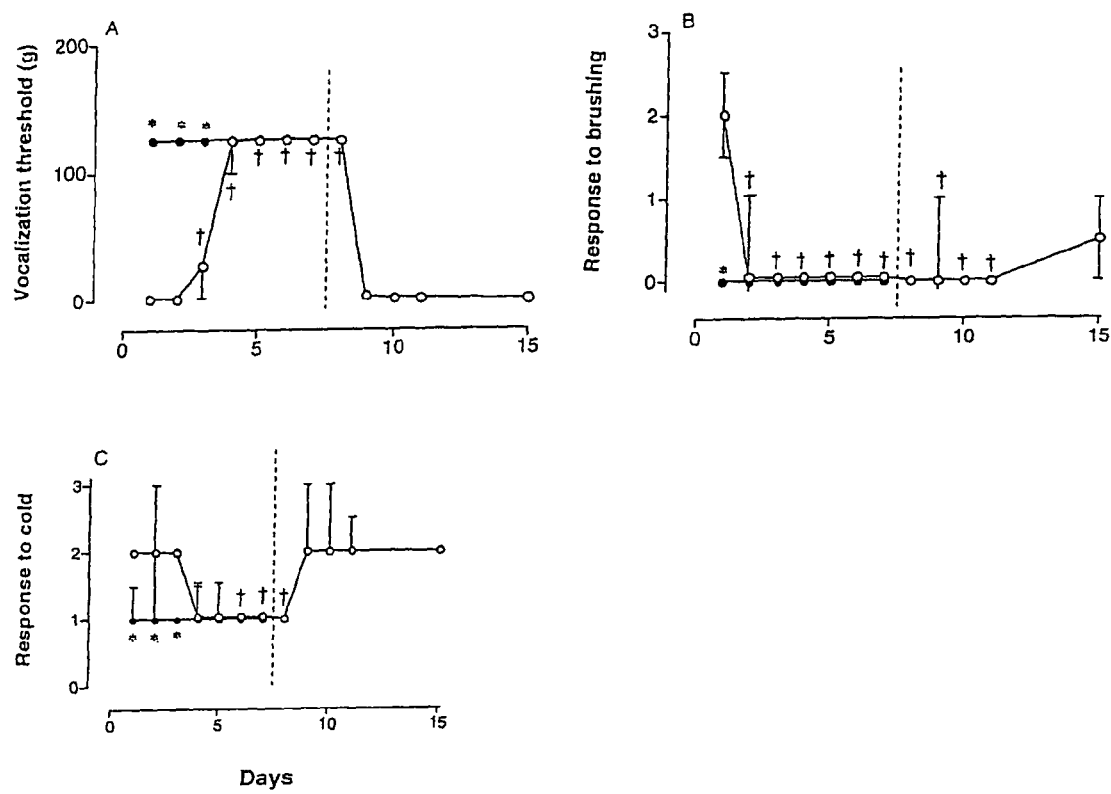

FIG. 2 shows the effect of 20 mg/kg SPM 927 injected twice daily on vocalization threshold to stimulation with von Frey hairs (A), brushing (B) and cold (C) in spinally injured rats. The rats were tested before and after the morning drug administration. The pre-drug threshold (open circles) and 1 h after drug administration (filled circles) are shown. The dashed line indicates the termination of administration of SPM 927. *=p<0.05 and **=<0.01 compared to pre-drug value on each day. †=p<0.05 and ††=p<0.01 compared to baseline value on day 1. The comparisons were made with Wilcoxon signed-ranks test (A-C).

The present invention is further illustrated the by the following Example.

EXAMPLE 1

SPM 927 alleviates neuropathic pain-like behaviours in an animal model for central neuropathic pain.

Materials and Methods

Male and female Sprague-Dawley rats (Möllegård, Denmark) weighing 200-250 g at the start of the experiments were used.

Photochemically-Induced Ischemic Spinal Cord Injury

Ischemic spinal cord injury was produced in female rats according to methods described previously (Xu et al., 1992). In brief, the rats were anesthetized with chloral hydrate (300 mg/kg, i.p.) and a midline incision was made on the skin overlying vertebral segments T12-L1. The animals were positioned beneath an argon laser beam and irradiated for 10 min with the beam directed towards vertebral segment T12 or T13 (spinal segments L3-5). Immediately prior to and 5 min after the start of the irradiation, erythrosin B (Red No 3, Aldrich-Chemie, Steinheim, Germany) dissolved in 0.9% saline was injected intravenously through the tail vein at a dose of 32.5 mg/kg. A tunable argon ion laser (Innova model 70, Coherent Laser Product Division, Palo Alto, Calif.) operating at 514 nm was used. The average beam output power was 160 mW. The beam covered the entire width of the vertebra and the length of the beam was 1-2 mm. After irradiation, the wound was closed in layers and the rats were allowed to recover. The bladder was emptied manually for 1 week.

Assessment of Mechanical and Cold Sensitivity after Spinal Cord Injury

The vocalization threshold to graded mechanical touch/pressure stimuli were tested with von Frey hairs. During testing the rats were gently restrained in a standing position and the von Frey hair was pushed onto the skin until the filament became bent. The frequency of stimulation was about 1/s and at each intensity the stimulus was applied 5-10 times. The intensity of stimulation which induced consistent vocalization (>75% response rate) was considered as pain threshold.

The response of rats to brushing stimulation was tested with the blunt point of a pencil gently stroking the skin on the trunk in a rostro-caudal direction. The frequency of the stimulation was about 1/s and responses were graded with a score of 0=no observable response; 1=transient vocalization and moderate effort to avoid probe; 2=consistent vocalization and aversive reactions and 3=sustained and prolonged vocalization and aggressive behaviours. Normal rats exhibited no reactions to brush stimuli (score 0).

Response to cold was tested with ethyl chloride spray applied to the shaved allodynic skin area. The response was graded with a score of 0=no observable response; 1=localized response (skin twitch and contraction), no vocalization; 2=transient vocalization, moderate struggle and 3=sustained vocalization and aggression.

Drugs and Statistics

SPM 927 was dissolved in physiological saline and injected intraperitoneally. The data for von Frey hairs, brushing and cold are expressed as median±median absolute deviation (M.A.D.) and analysed with Wilcoxon signed-ranks test or paired t-test.

Results

Effects of a Single Dose of SPM 927 on Allodynia-Like Behaviours in Spinally Injured Rats SPM 927 at 10 mg/kg had no effect whereas at 15 mg/kg it partially alleviated mechanical and cold allodynia in the majority, but not all, rats (FIG. 1). The increase in threshold to stimulation with von Frey hairs after 15 mg/kg was significant, but did not return to normal level (FIG. 1a). A significant effect on brushing and cold was also seen at this dose (FIG. 1B, C). SPM 927 at 20 mg/kg completely reversed mechanical and cold allodynia in all rats for about 2 h (FIG. 1).

Effects of Repeated Administration of SPM 927 in Spinally Injured Rats

The animals were injected with 20 mg/kg SPM 927 twice a day. The pre-drug response and the response 1 h after injection were assessed in the morning session. On days 1-3 SPM 927 produced an increase in vocalization threshold to von Frey hair stimulation, similar to the single injection experiments (FIG. 2A). Interestingly, the pre-drug response to von Frey hair stimulation was normalized on day 4 (FIG. 2A). The baseline responses to brushing (FIG. 2B) and cold (FIG. 2C) were also normalized from day 2 to day 6 respectively. The normalization of basal sensitivity lasted at least 8 days without signs of tolerance. Administration of SPM 927 was discontinued after day 7 and the allodynia to stimulation with von Frey hairs and cold reappeared on day 9, but the effect on brush stimulation was maintained up to day 11 (FIG. 2).

REFERENCES

Hao, J.-X., Xu, X.-J., Urban, L. And Wiesenfeld-Hallin, Z., Repeated administration of systemic gabapentin alleviates allodynia-like behaviours in spinally injured rats, *Neurosci. Lett.,* 2000, 280, 211-214.

von Heijne, M., Hao, J.-X., Yu, W., Sollevi, A., Xu, X.-J., Wiesenfeld-Hallin, Z., Tolerance to the anti-allodynic effect of intrathecal r-phenylisopropyladenosine in a rat model of ischemic spinal cord lesion: lack of ross-tolerance with morphine, *Anesth Analg.,* 1998; 87:1367-1371.

Xu, X.-J., Hao, J.-X., Aldskogius, H., Seiger, Å., Wiesenfeld-Hallin, Z. Chronic pain-realted syndrome in rats after ischemic spinal cord lesion: a possible animal model for pain in patients with spinal cord injury. *Pain,* 1992; 48: 279-290.

Yezierski R P and Burchiel, K J (Eds), *Spinal Cord Injury Pain: Assessment, Mechanisms, Management.* IASP Press, Seattle.

Yu, W., Hao, J. X., Xu, X.-J., Wiesenfeld-Hallin, Z. The development of morphine tolerance and dependence in rats with chronic pain. *Brain Res* 1997a; 756:141-146.

Yu, W., J.-X., Xu, X.-J., Wiesenfeld-Hallin, Z. Comparison of the anti-allodynic and antinociceptive effects of systemic, intrathecal and intracerebroventricular morphine in a rat model of central neuropathic pain, *Europ J Pain* 1997b; 1: 17-29.

The invention claimed is:

1. A method for treating central neuropathic pain in a subject, comprising administering to the subject the compound (R)-2-acetamido-N-benzyl-3-methoxypropionamide or a pharmaceutically acceptable salt thereof, in a dosage amount of about 50 mg to about 600 mg per day for a period of at least one week.

2. The method of claim 1, wherein the compound is substantially enantiopure.

3. A method for reducing the susceptibility of a subject to central neuropathic pain, the method comprising administering to the subject the compound (R)-2-acetamido-N-benzyl-3-methoxypropionamide or a pharmaceutically acceptable salt thereof, wherein the subject has a central lesion and/or a disease associated with central neuropathic pain.

4. The method of claim 1, wherein the central neuropathic pain is spinal cord injury pain.

5. The method of claim 1, wherein the compound is administered in a dosage effective, upon passing the subject's blood-brain barrier, to provide an amount of the compound in the brain effective for the treatment of central neuropathic pain.

6. The method of claim 1, wherein the dosage amount administered is about 100 mg to about 600 mg per day.

7. The method of claim 1, wherein the dosage amount administered is about 200 mg to about 600 mg per day.

8. The method of claim 1, wherein the compound is administered in no more than three doses per day.

9. The method of claim 1, wherein the compound is administered in a pharmaceutical composition resulting in a plasma concentration of the compound of about 0.1 to about 15 µg/ml (trough) and about 5 to about 18.5 µg/ml (peak).

10. The method of claim 1, wherein the central neuropathic pain is associated with infarction, a compressive tumor or abscess, Parkinson's disease, spinal cord injury, an inflammatory central nervous system disease, ischemia, hemorrhage, arteriovenous malformation and/or syringomyelia.

11. The method of claim 1, wherein the central neuropathic pain is associated with an inflammatory central nervous system disease selected from multiple sclerosis, myelitis and syphilis.

12. The method of claim 3, wherein the compound is substantially enantiopure.

13. The method of claim 3, wherein the compound is administered for a period of at least one week.

14. The method of claim 3, wherein the compound is administered in a dosage effective, upon passing the subject's blood-brain barrier, to provide an amount of the compound in the brain effective for reducing the susceptibility of a subject to central neuropathic pain.

15. The method of claim 3, wherein the compound is administered in a dosage amount of about 50 mg to about 600 mg per day.

16. The method of claim 3, wherein the dosage amount administered is about 100 mg to about 600 mg per day.

17. The method of claim 3, wherein the dosage amount administered is about 200 mg to about 600 mg per day.

18. The method of claim 3, wherein the compound is administered in no more than three doses per day.

19. The method of claim 3, wherein the compound is administered in a pharmaceutical composition resulting in a plasma concentration of the compound of about 0.1 to about 15 µg/ml (trough) and about 5 to about 18.5 µg/ml (peak).

20. The method of claim 3, wherein the central neuropathic pain is associated with infarction, a compressive tumor or abscess, Parkinson's disease, spinal cord injury, an inflammatory central nervous system disease, ischemia, hemorrhage, arteriovenous malformation and/or syringomyelia.

21. The method of claim 3, wherein the central neuropathic pain is associated with an inflammatory central nervous system disease selected from multiple sclerosis, myelitis and syphilis.

22. A method for treating central neuropathic pain in a subject, comprising administering to the subject the compound (R)-2-acetamido-N-benzyl-3-methoxypropionamide or a pharmaceutically acceptable salt thereof, in a dosage amount of about 50 mg to about 600 mg per day; wherein the central neuropathic pain is associated with infarction, Parkinson's disease, an inflammatory central nervous system disease, ischemia, hemorrhage, arteriovenous malformation and/or syringomyelia.

23. The method of claim 22, wherein the compound is administered for a period of at least one week.

24. The method of claim 22, wherein the compound is substantially enantiopure.

25. The method of claim 22, wherein the compound is administered in a dosage effective, upon passing the subject's blood-brain barrier, to provide an amount of (R)-2-acetamido-N-benzyl-3-methoxypropionamide in the brain effective for the treatment of central neuropathic pain.

26. The method of claim 22, wherein the dosage amount administered is about 100 mg to about 600 mg per day.

27. The method of claim 22, wherein the dosage amount administered is about 200 mg to about 600 mg per day.

28. The method of claim 22, wherein the compound is administered in no more than three doses per day.

29. The method of claim 22, wherein the compound is administered in a pharmaceutical composition resulting in a plasma concentration of the compound of about 0.1 to about 15 µg/ml (trough) and about 5 to about 18.5 µg/ml (peak).

30. The method of claim 22, wherein the central neuropathic pain is associated with an inflammatory central nervous system disease selected from multiple sclerosis, myelitis and syphilis.

31. The method of claim 1, wherein the compound is (R)-2-acetamido-N-benzyl-3-methoxypropionamide.

32. The method of claim 3, wherein the compound is (R)-2-acetamido-N-benzyl-3-methoxypropionamide.

* * * * *

UNITED STATES PATENT AND TRADEMARK OFFICE
CERTIFICATE OF CORRECTION

PATENT NO. : 7,794,987 B2  Page 1 of 1
APPLICATION NO. : 11/000951
DATED : September 14, 2010
INVENTOR(S) : Thomas Stoehr It is certified that error appears in the above-identified patent and that said Letters Patent is hereby corrected as shown below:

Column 4, line 54, "GABAB$_8$" should be changed to -- GABA$_B$ --.

Column 6, line 21, "NR$_{16}$" should be changed to -- NR'$_6$ --.

Column 6, line 30, "N+R$_5$R$_6$R$_7$" should be changed to -- N$^+$R$_5$R$_6$R$_7$ --.

Column 6, line 33, " 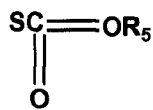 " should be changed to -- 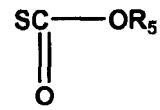 --.

Column 9, line 23, "R$_5$R$_6$" should be changed to -- R$_5$ R$_6$ --.

Column 9, line 50, "O—R$_{60}$" should be changed to -- O—R$_{50}$ --.

Column 11, line 43, "NR$_4$OR" should be changed to -- NR$_4$OR$_5$ --.

Signed and Sealed this
Fifteenth Day of March, 2011

David J. Kappos
*Director of the United States Patent and Trademark Office*